(12) United States Patent
Kim et al.

(10) Patent No.: US 11,214,531 B2
(45) Date of Patent: Jan. 4, 2022

(54) ALPHAOLEFIN OLIGOMER HAVING UNIFORM STRUCTURE AND METHOD OF PREPARING SAME

(71) Applicant: DL Chemical CO., LTD., Seoul (KR)

(72) Inventors: So Han Kim, Daejeon (KR); Tae Hee Lee, Daejeon (KR); Jae Hoon Uhm, Daejeon (KR)

(73) Assignee: DL Chemical CO., LTD., Seoul (KR)

(*) Notice: Subject to any disclaimer, the term of this patent is extended or adjusted under 35 U.S.C. 154(b) by 50 days.

(21) Appl. No.: 16/688,210

(22) Filed: Nov. 19, 2019

(65) Prior Publication Data
US 2020/0207688 A1  Jul. 2, 2020

(30) Foreign Application Priority Data

Dec. 28, 2018 (KR) .................. 10-2018-0171965

(51) Int. Cl.
*C07C 9/16* (2006.01)
*C07C 9/22* (2006.01)
(Continued)

(52) U.S. Cl.
CPC .................. *C07C 9/16* (2013.01); *C07C 9/22* (2013.01); *C10M 105/04* (2013.01); *C10M 2203/022* (2013.01); *C10N 2020/02* (2013.01); *C10N 2020/04* (2013.01); *C10N 2020/071* (2020.05); *C10N 2020/085* (2020.05)

(58) Field of Classification Search
CPC .... C07C 9/16; C07C 9/22; C07C 2/34; C07C 7/04; C07C 5/03; C07C 2531/22; C07C 2/32; C10M 105/04; C10M 2203/022; C10M 107/10; C10M 2205/0285; C10M 107/02; C10M 2205/003; C10N 2020/071; C10N 2020/085; C10N 2020/02; C10N 2020/04; C10N 2020/06; C10N 2030/08; C10N 2030/10; C08F 10/14

See application file for complete search history.

(56) References Cited

U.S. PATENT DOCUMENTS 5,104,579 A * 4/1992 Benjamin ............ C10M 101/02
508/270
2009/0163391 A1* 6/2009 Zakarian ............. C10M 171/02
508/133
(Continued)

FOREIGN PATENT DOCUMENTS

JP    2008-163216 A    7/2008
JP    2018-519394 A    7/2018
(Continued)

OTHER PUBLICATIONS

Communication dated Nov. 17, 2020 by the Japanese Patent Office in application No. 2019-208952.
(Continued)

*Primary Examiner* — Ali Z Fadhel
(74) *Attorney, Agent, or Firm* — Sughrue Mion, PLLC (57) ABSTRACT

The present invention relates to an alphaolefin oligomer having a uniform structure and a method of preparing the same, in which the alphaolefin oligomer has a uniform molecular structure with a low branch ratio, thereby exhibiting improved thermal and oxidative stability, a long service life, low volatility, a low pour point and a high viscosity index.

13 Claims, 2 Drawing Sheets

(51) Int. Cl.
*C10M 105/04* (2006.01)
*C10N 20/00* (2006.01)
*C10N 20/02* (2006.01)
*C10N 20/04* (2006.01)

(56) References Cited

U.S. PATENT DOCUMENTS

2010/0087349 A1* 4/2010 Lee .................. C10M 111/04
508/499
2017/0226441 A1* 8/2017 Courtiade ............ C10M 107/10
2018/0371348 A1* 12/2018 Oumar-Mahamat .........................
C10M 105/04

FOREIGN PATENT DOCUMENTS

| KR | 10-2008-0069181 A | 7/2008 |
| KR | 10-2010-0097191 A | 9/2010 |
| KR | 10-2015-0038437 A | 4/2015 |
| WO | 2010053022 A1 | 5/2010 |
| WO | 2013024701 A1 | 2/2013 |

OTHER PUBLICATIONS

Communication dated Jun. 5, 2020 by the European Patent Office in application No. 19209254.2.
Communication dated Sep. 7, 2020 by the Patent Office of the Cooperation Council for the Arab States of the Gulf in application No. GC 2019-38665.
James A. Brennan et al., "Wide-Temperature Range Synthetic Hydrocarbon Fluids", Ind. Eng. Chem. Prod. Res. Dev. 1980, pp. 2-6, vol. 19, No. 1.
A. S. Sarpal et al., "Correlation of structure and properties of groups I to III base oils", Lubrication Science 2012, pp. 199-215, 24.
Communication dated Feb. 24, 2021 by the Japanese Patent Office in application No. 2019-208952.

* cited by examiner

ALPHAOLEFIN OLIGOMER HAVING UNIFORM STRUCTURE AND METHOD OF PREPARING SAME

CROSS-REFERENCE TO RELATED APPLICATIONS

This application is based on and claims priority from Korean Patent Application No. 10-2018-0171965, filed on Dec. 28, 2018 with the Korean Intellectual Property Office, the disclosure of which is incorporated herein in its entirety by reference.

BACKGROUND OF THE INVENTION

1. Technical Field

The present invention relates to an alphaolefin oligomer having a uniform structure and a method of preparing the same, and more particularly to an oligomer product, which includes a mixture of varying amounts of dimers, trimers, tetramers, pentamers and higher-order oligomers, and which is hydrogenated and exhibits improved thermal and oxidative stability, a long service life, low volatility, a low pour point and a high viscosity index and may thus be utilized for a lubricant in a variety of fields, and a method of preparing the same.

2. Description of the Related Art

In general, a lubricant is composed of a lubricant base oil and additives for improving the properties thereof, and lubricant base oil is typically divided into mineral oil and synthetic oil. Mineral oil refers to naphthenic oil produced in the process of separating and refining crude oil, and synthetic oil refers to polyalphaolefins (PAOs) produced by polymerizing alphaolefins produced during refining of petroleum.

Conventionally, mineral oil is mainly used as lubricant base oil, but as industry develops, lubricants having high performance are required in order to withstand the high performance, high power output, and harsh operating conditions of internal combustion engines and industrial machinery. Recently, the demand for polyalphaolefin having high shear stability and enabling use thereof in a wide range of environmental conditions, particularly at low temperatures, is increasing because of the high viscosity index and superior fluidity thereof at low temperatures compared to lubricant base oil produced from mineral oil. For decades, polyalphaolefin synthetic lubricants have been commercially produced through extensive and intensive research and development, and industrial studies are also actively underway to improve the performance of synthetic lubricants based on oligomerization of C6-C20 alphaolefin.

The present inventors have also studied to produce alphaolefin oligomers having superior properties and have focused on the correlation between oligomer structures having similar carbon numbers produced from various alphaolefins and the properties thereof such as viscosity index, etc. disclosed in Ind. Eng. Chem. Prod. Res. Dev. 1980, 19, 2-6 published by Brennan et. al. and the correlation between molecular structures and viscosity-temperature behavior in lubricant systems disclosed in Lubrication Science 2012, 24, 199-215 by Saff et. al., and thus have developed alphaolefin oligomers having uniform molecular structures to thereby exhibit improved specific factors, such as viscosity index, Noack volatility, flash point, and the like, and preparation methods thereof.

CITATION LIST

Patent Literature (Patent Document 1) Korean Patent Application Publication No. 10-2010-0097191

SUMMARY OF THE INVENTION

Accordingly, an objective of the present invention is to provide an alphaolefin oligomer suitable for use in lubricant base oil, which exhibits a low Noack volatility, a high flash point and a high viscosity index.

Another objective of the present invention is to provide a method of preparing an alphaolefin oligomer having a uniform molecular structure in order to achieve the above physical properties.

In order to accomplish the above objectives, the present invention provides an alphaolefin oligomer having a uniform molecular structure with a low branch ratio.

Specifically, the alphaolefin oligomer of the present invention may have a branch ratio of 0.265 or less, preferably 0.25 or less, and more preferably 0.24 or less, as represented by Equation (1) below.

$$\text{Branch ratio} = P1/P2 \quad (1)$$

(wherein P1 is the amount of a $CH_3$ group and P2 is the amount of a $CH_2$ group, the amounts of $CH_2$ and $CH_3$ groups being measured through $^1$H-NMR)

The alphaolefin oligomer is configured such that the carbon at position B1 in Structural Formula 1 below has a $T_1$ relaxation time of less than 1.0 at 298 K as measured by an NMR pulse sequence, the carbon at position B2 has a $T_1$ relaxation time of less than 0.6, and the carbon at position B3 has a $T_1$ relaxation time of less than 0.5. Here, the carbon at position B3 may be tertiary carbon (CH group) or secondary carbon ($CH_2$ group). Also, the carbon at position A1 has a $T_1$ relaxation time of 2.35 or more and the carbon at position A2 has a $T_1$ relaxation time of 2.2 or more.

[Structural Formula 1]

(wherein n=1 to 9)

The alphaolefin oligomer of the present invention may have a flash point of 235° C. or more and a Noack volatility of less than 12%.

The kinematic viscosity at 100° C. may be 6.3 cSt or less, and the kinematic viscosity at 40° C. may be 35.0 cSt or less.

The alphaolefin oligomer may have a viscosity index of 130 or more and a pour point of −50° C. or less, preferably −70° C. or less.

The alphaolefin oligomer may have a number average molecular weight of 1100 or less and a weight average molecular weight of 1300 or less. Here, the alphaolefin oligomer may have a molecular weight distribution (Mw/Mn) of 1.0 to 3.0.

The alphaolefin oligomer may be mixed with a fluid selected from the group consisting of mineral oil serving as lubricant base oil, a dispersant, an antioxidant, an antiwear agent, a defoamer, a corrosion inhibitor, a detergent, a seal swelling agent, a viscosity enhancer and combinations thereof, and may thus be provided in the form of a lubricant composition.

The alphaolefin oligomer of the present invention may be configured such that the molecular structure thereof is uniformly controlled by minimizing isomerization using a homogeneous metallocene catalyst.

In the present invention, the metallocene catalyst may be composed of a metallocene compound (A), an activator compound (B) and an ion activator compound (C).

Here, the metallocene compound (A) may be at least one selected from the group consisting of Chemical Formulas 1 to 6

[Chemical Formula 1]

[Chemical Formula 2]

[Chemical Formula 3]

[Chemical Formula 4]

In Chemical Formulas 1 to 4,

M is a transition metal selected from the group consisting of titanium, zirconium, and hafnium, B is a linker such as a C1-C20 alkylene group, a C6-C20 arylene group, C1-C20 dialkyl silicon, C1-C20 dialkyl germanium, a C1-C20 alkylphosphine group or a C1-C20 alkylamine group or is in a form having no linker, $X_1$ and $X_2$ are the same as or different from each other, and are each independently a halogen atom, a C1-C20 alkyl group, a C2-C20 alkenyl group, a C2-C20 alkynyl group, a C6-0.7 C20 aryl group, a C7-C40 alkylaryl group, a C7-C40 arylalkyl group, a C1-C20 alkylamido group, a C6-C20 arylamido group, a C1-C20 alkylidene group or a C1-C20 alkoxy group, and $R_1$ to $R_{10}$ are the same as or different from each other, and are each independently hydrogen, a C1-C20 alkyl group, a C2-C20 alkenyl group, a C6-C20 aryl group, a C7-C20 alkylaryl group, a C7-C20 arylalkyl group, a C5-C60 cycloalkyl group, a C4-C20 heterocyclic group, a C1-C20 alkynyl group, or a hetero group or a silyl group including a C6-C20 aryl group.

[Chemical Formula 5]

[Chemical Formula 6]

In Chemical Formulas 5 and 6,

M is a transition metal selected from the group consisting of titanium, zirconium, and hafnium, B is a linker such as a C1-C20 alkylene group, a C6-C20 arylene group, C1-C20 dialkyl silicon, C1-C20 dialkyl germanium, a C1-C20 alkylphosphine group or a C1-C20 alkylamine group or is in a form having no linker, $X_1$ and $X_2$ are the same as or different from each other, and are each independently a halogen atom, a C1-C20 alkyl group, a C2-C20 alkenyl group, a C2-C20 alkynyl group, a C6-C20 aryl group, a C7-C40 alkylaryl group, a C7-C40 arylalkyl group, a C1-C20 alkylamido group, a C6-C20 arylamido group, a C1-C20 alkylidene group or a C1-C20 alkoxy group, and $R_1$ to $R_{10}$ are the same as or different from each other, and are each independently hydrogen, a C1-C20 alkyl group, a C2-C20 alkenyl group, a C6-C20 aryl group, a C7-C20 alkylaryl group, a C7-C20 arylalkyl group, a C5-C60 cycloalkyl group, a C4-C20 heterocyclic group, a C1-C20 alkynyl group, or a hetero group or a silyl group including a C6-C20 aryl group.

$R_{11}$, $R_{13}$ and $R_{14}$ are the same as each other and are hydrogen, and $R_{12}$s are the same as or different from each other and are each independently hydrogen, a C1-C20 alkyl group, a C2-C20 alkenyl group, a C6-C20 aryl group, a C7-C20 alkylaryl group, a C7-C20 arylalkyl group, a C5-C60 cycloalkyl group, a C4-C20 heterocyclic group, a C1-C20 alkynyl group, or a hetero group or a silyl group including a C6-C20 aryl group.

The metallocene compound of Chemical Formulas 2 to 6 may also include a compound substituted through hydrogenation, a preferred example of which is dimethylsilyl bis (tetrahydroindenyl) zirconium dichloride.

The activator compound (B) is a compound that reacts with the metallocene compound (A) or derivatives thereof to form an ionic compound, and may be at least one compound selected from the group consisting of dimethylanilinium tetrakis(perfluorophenyl) borate and triphenyl carbonium tetrakis(perfluorophenyl) borate.

The ion activator compound (C) may be used in combination with an assistant activator including a trialkyl aluminum, such as trimethyl aluminum, triethyl aluminum, triisopropyl aluminum, dimethyl ethyl aluminum, triisobutyl aluminum, and trioctyl aluminum, an alkyl aluminum halide, such as dimethyl aluminum chloride, diethyl aluminum chloride, methyl aluminum dichloride, ethyl aluminum dichloride, dimethyl aluminum fluoride, diisobutyl aluminum hydride, diethyl aluminum hydride, and ethyl aluminum sesquichloride, dimethylaluminum, or an aluminoxane such as methylaluminoxane, which may be used alone or in combinations of two or more thereof.

In the metallocene catalyst of the present invention, the metallocene compound (A) and the activator compound (B) may be used at a molar ratio of 10:1 to 1:100, and preferably 2:1 to 1:10.

When using the ion activator compound (C), the molar ratio of the metallocene compound (A) and the ion activator compound (C) may be 1:1 to 1:10,000, and preferably 1:5 to 1:1,000. If the molar ratio of these compounds is less than 1:1, the catalyst compound is not completely alkylated due to the small amount of the ion activator compound. On the other hand, if the molar ratio thereof exceeds 1:10,000, incomplete activation may be caused by side reactions between compounds.

Since the alphaolefin monomers are sensitive to water, it is important to control water contained therein for reasons such as catalyst poisons and the like. The ion activator compound (C) is used as a scavenger in order to reduce the effect of water on the polymerization reaction. The water and the ion activator compound (C) are used at a molar ratio of 1:1 to 1:1,000, and preferably 1:1 to 1:100.

In the present invention, a hydrocarbon solvent such as pentane, hexane, heptane, etc., or an aromatic solvent such as benzene, toluene, xylene, etc. may be used as the reaction solvent in the preparation of the metallocene catalyst, but the present invention is not limited thereto. Any solvent that is useful in the preparation may be used.

The alphaolefin monomer of the present invention includes a C2-C20 aliphatic olefin, specific examples of which may include ethylene, propylene, 1-butene, 1-pentene, 3-methyl-1-butene, 1-hexene, 4-methyl-1-pentene, 3-methyl-1-pentene, 1-heptene, 1-octene, 1-decene, 1-dodecene, and 1-tetradecene. These monomers may be used alone or in combinations of two or more thereof. Here, isomers thereof may also be included. In copolymerization, the amount of the monomer is 1 to 95 mol %, and preferably 5 to 90 mol %.

The alphaolefin oligomer polymerization of the present invention may be carried out through liquid polymerization, slurry polymerization, bulk polymerization, or gas polymerization in the presence of the hydrocarbon solvent. A C5-C20 aliphatic hydrocarbon solvent such as pentane, hexane, heptane, nonane and decane and isomers thereof, an aromatic hydrocarbon solvent such as toluene, benzene and xylene, and a halogen-atom-containing hydrocarbon solvent such as chlorobenzene may be used alone or in combinations of two or more thereof so that the reaction may be carried out while maintaining the low viscosity at the initial stage of the reaction. The polymerization may be carried out in a batch, semi-continuous or continuous manner in a batch reactor, a loop reactor and the like, either alone or in combination.

The alphaolefin oligomerization is carried out in the presence of an inert gas such as argon or nitrogen at a temperature of 15 to 200° C. The molar ratio of metallocene catalyst to alphaolefin may be 1:1,000-1:1,000,000, and preferably 1:5,000-1:1,000,000, and the reaction time may fall in the range of 10 min to 48 hr.

The oligomer produced by the oligomerization of alphaolefin may be subjected to simple distillation through vacuum distillation at a pressure of 0.1 to 50 torr in the temperature range of 80 to 450° C.

Moreover, as a post-treatment process performed after the alphaolefin oligomerization, the reaction is usually terminated with water or an alcohol, and the catalyst is quenched using an aqueous alkali solution.

In the present invention, the alphaolefin oligomer has a double bond, which remains during oligomerization. Since this double bond has a negative effect upon use as a lubricant or engine oil, it is hydrogenated and thus saturated. The catalyst used in the hydrogenation process includes a Ni or Co catalyst or a noble metal catalyst such as Pd or Pt.

The polyalphaolefin prepared using the metallocene catalyst has a more regular structure than those prepared using cation catalysts. Here, the molecular structure of a decene oligomer may be determined by measuring the $T_1$ relaxation time, which is associated with molecular mobility, through nuclear magnetic resonance (NMR) spectroscopy. The $T_1$ relaxation time in the low-molecular-weight range is high with an increase in mobility but is low with a decrease in mobility. Briefly, high mobility means that the molecular structure is complex and irregular. In this regard, the alphaolefin oligomer of the present invention is characterized by having a more regular molecular structure in that the terminal carbon of the prepared oligomer represents a high $T_1$ relaxation time and the central carbon thereof represents a low $T_1$ relaxation time.

In order to improve the selectivity of alphaolefin oligomer products of the present invention, facilitate the decene addition reaction and minimize the isomerization reaction, a metallocene compound including a ligand added with one or two hydrogens, a large-volume ligand, a small-volume ligand, and a ligand combination thereof may be used. Taking into consideration the selectivity of the main component of the alphaolefin oligomer of the present invention, kinematic viscosity at 100° C. before separation is 2 to 7 cSt. Less isomerization of the product occurs during the separation process after the hydrogenation reaction, and the product is easily separated.

According to the present invention, the method of preparing the alphaolefin oligomer is capable of minimizing the formation of chain branches that deteriorate the properties of lubricant base oil, thereby realizing an alphaolefin oligomer having a uniform molecular structure with a low branch ratio and thus improved thermal and oxidative stability, a long service life, low volatility, a low pour point and a high viscosity index. Therefore, the preparation of polyalphaolefin that can be applied to lubricants in various fields becomes possible.

DESCRIPTION OF SPECIFIC EMBODIMENTS

Hereinafter, a detailed description will be given of the preferred embodiments of the present invention. However, the present invention is not limited to these embodiments, but may be modified in other forms. These embodiments are provided in order to fully convey the spirit of the present invention to those skilled in the art so that the contents introduced herein are thorough and complete.

Example 1: Preparation of Oligomer Using Metallocene Catalyst—Simple Distillation and then Hydrogenation 1. Oligomerization 530 ml (392 g) of decene was placed in a 1 L stainless steel autoclave reactor and then maintained at 110° C. In this procedure, as necessary, the polymerization temperature was adjusted to the range of 50 to 150° C., and 1 mmol of triisobutylaluminum was added, or was not added if not needed. Thereafter, the already prepared catalyst (including 0.01 mmol of a metallocene catalyst, 0.012 mmol of a promoter, 0.6 mmol of triisobutylaluminum and 6 ml of toluene) was placed in the reactor. Subsequently, the reaction was carried out for 3 hr with stirring at 700 rpm, after which the reaction was terminated by the addition of 400 ml of a 10% sodium hydroxide aqueous solution. Next, the upper organic layer was extracted, and unreacted decene and decene isomers as byproducts were stripped and removed, thereby obtaining a decene oligomer.

2. Simple Distillation of Oligomer 150 ml of the decene oligomer prepared above was placed in a 2 L flask with a 5-30 cm Vigreux distillation column and was then maintained in a vacuum to remove oxygen. Thereafter, vacuum distillation was conducted at a pressure of 0.45 torr and a temperature of 170 to 230° C., after which the residue was cooled to room temperature in a vacuum in order to prevent pyrolysis thereof.

3. Hydrogenation of Oligomer 140 g of 5 wt % palladium/alumina was placed in a 1 L Parr reactor, and 0.5 L of the decene oligomer separated above was added thereto and purged with nitrogen at 120° C. for 30 min. Thereafter, the temperature was elevated to 180° C. and the reaction was initiated under a hydrogen pressure of 2 MPa and was then terminated after 4 hr.

Example 2: Preparation of Oligomer Using Metallocene Catalyst—Hydrogenation and then Simple Distillation 1. Oligomerization 100 wt % of hexane was placed in a 1 L stainless steel autoclave reactor and then maintained at 110° C. In this procedure, as necessary, the polymerization temperature and the amount of added hexane were adjusted to 50-150° C. and 0-100 wt %, respectively. Thereafter, the already prepared catalyst (including 0.4 mmol of a metallocene catalyst, 0.5 mmol of a promoter, 1.1 mmol of triisobutylaluminum and 350 ml of toluene) was placed at 0.2-0.3 ml/min in the reactor, and simultaneously, decene was added at 5.0-7.0 ml/min. Subsequently, the reaction was carried out for 3 hr with stirring at 1200 rpm, after which the reaction was terminated by the addition of 400 ml of a 10% sodium hydroxide aqueous solution. Next, the upper organic layer was extracted, and unreacted decene and decene isomers as byproducts were stripped and removed, thereby obtaining a decene oligomer.

2. Hydrogenation and Simple Distillation of Oligomer

The same procedures as in Example 1 were performed, with the exception that the prepared oligomer was first hydrogenated and then subjected to simple distillation, unlike Example 1.

Example 3: Preparation of Oligomer Using Metallocene Catalyst—Hydrogenation and then Simple Distillation 1. Oligomerization The oligomerization was performed in the same manner as in Example 2.

2. Hydrogenation and Simple Distillation of Oligomer

The same procedures as in Example 2 were performed, with the exception that vacuum distillation was conducted at a pressure of 0.45 torr and a temperature of 260 to 290° C. upon simple distillation of the oligomer, unlike Example 2.

Comparative Example 1: Preparation of Oligomer Using Cation Catalyst—Simple Distillation and then Hydrogenation A decene oligomer was prepared using a cation catalyst, unlike the above Examples.

Specifically, 135 ml (100 g) of decene was placed in a 1 L stainless steel autoclave reactor and the polymerization temperature was then maintained at 10 to 20° C. Subsequently, a cation catalyst ($ACl_3$, $BF_3$, etc.) complexed with an alcohol was added at 0.8 mmol/100 g into the reactor. Thereafter, the reaction was carried out for 2 hr in a nitrogen atmosphere with stirring at 700 rpm, after which the reaction was terminated by the addition of dilute ammonium hydroxide at a temperature of 80 to 90° C. Then, the upper organic layer was extracted, and unreacted decene and decene isomers as byproducts were stripped and removed, thereby obtaining a decene oligomer. The simple distillation of the prepared oligomer and the hydrogenation of the decene oligomer were performed in the same manner as in Example 1, with the exception that vacuum distillation was conducted at a temperature of 160 to 220° C. upon simple distillation.

Comparative Example 2: Preparation of Oligomer Using Cation Catalyst—Hydrogenation and then Simple Distillation An oligomer was prepared in the same manner as in Comparative Example 1, after which the prepared oligomer was subjected to hydrogenation and then simple distillation, unlike Comparative Example 1.

Evaluation of Properties

The properties of the alphaolefin oligomers prepared in Examples 1 to 3 and Comparative Examples 1 and 2 were measured as follows.

1. Measurement of Molecular Weight

The molecular weights of the oligomers of Examples 1 to 3 and Comparative Examples 1 and 2 were measured through gel permeation chromatography (GPC). The results are shown in Table 1 below.

TABLE 1

|  | Mn | Mw | Mz | Mw/Mn |
| --- | --- | --- | --- | --- |
| Example 1 | 702 | 725 | 752 | 1.033 |
| Example 2 | 665 | 697 | 740 | 1.049 |
| Example 3 | 900 | 936 | 972 | 1.040 |
| Comparative Example 1 | 666 | 691 | 720 | 1.037 |
| Comparative Example 2 | 625 | 650 | 679 | 1.039 |

2. Measurement of Viscosity Index, Pour Point, Flash Point and Noack Volatility

The VI (viscosity index; ASTM D445), pour point (ASTM D97), flash point (ASTM D92), bromine number and Noack volatility (ASTM D5800) of the alphaolefin oligomers of Examples 1 to 3 and Comparative Examples 1 and 2 were measured. The results are shown in Table 2 below.

TABLE 2

|  | Example 1 | Example 2 | Example 3 | Comparative Example 1 | Comparative Example 2 |
| --- | --- | --- | --- | --- | --- |
| Viscosity @100° C. (cSt) | 3.90 | 4.06 | 6.01 | 4.13 | 4.06 |
| Viscosity @40° C. | 16.54 | 17.41 | 30.54 | 18.50 | 17.82 |
| Viscosity Index | 134.1 | 136.1 | 147.2 | 127.3 | 129.7 |
| Pour point (° C.) | −72 | −75 | −75 | −74 | −72 |
| Flash point (° C.) | 240 | 242 | 248 | 234 | 230 |
| Noack vol. (%) | 11.31 | 10.15 | 6.73 | 12.88 | 13.71 |
| Bromine No. (g/100 g) | 0.25 | 0.18 | 0.26 | 0.57 | 0.24 |

As is apparent from Table 2, the properties of the alphaolefin oligomers of Examples were superior to those of the alphaolefin oligomers of Comparative Examples, which is deemed to be due to the difference in the molecular structure of the alphaolefin formed during the polymerization.

Specifically, the oligomers prepared in Examples had a uniform molecular structure with a low branch ratio, containing no tertiary hydrogen due to isomerization, and were thus improved in properties such as viscosity index, flash point, pour point and Noack volatility.

3. Measurement of $T_1$ Relaxation Time

Using 500 MHz NMR (Bruker AVANCE III) with a BBO probe, the $T_1$ relaxation time at 298 K of the oligomers of Examples 1 to 3 and Comparative Examples 1 and 2 was measured. Specifically, 0.1 g of a decene oligomer and 1 ml of a deuterium solvent (chloroform) were placed in an NMR tube, after which measurement was performed through hydrogen and carbon NMR spectra, DEPT (Distortion-less Enhanced by Polarization Transfer), COSY (Correlation Spectroscopy), HSQC (Heteronuclear Single-Quantum Correlation Spectroscopy) and HMBC (Heteronuclear Multiple-Bond Correlation Spectroscopy). The spectral results were analyzed and the carbon peak for each structure is shown in Table 3 below, and the measured $T_1$ relaxation time is shown in Table 4 below.

Figure 1:
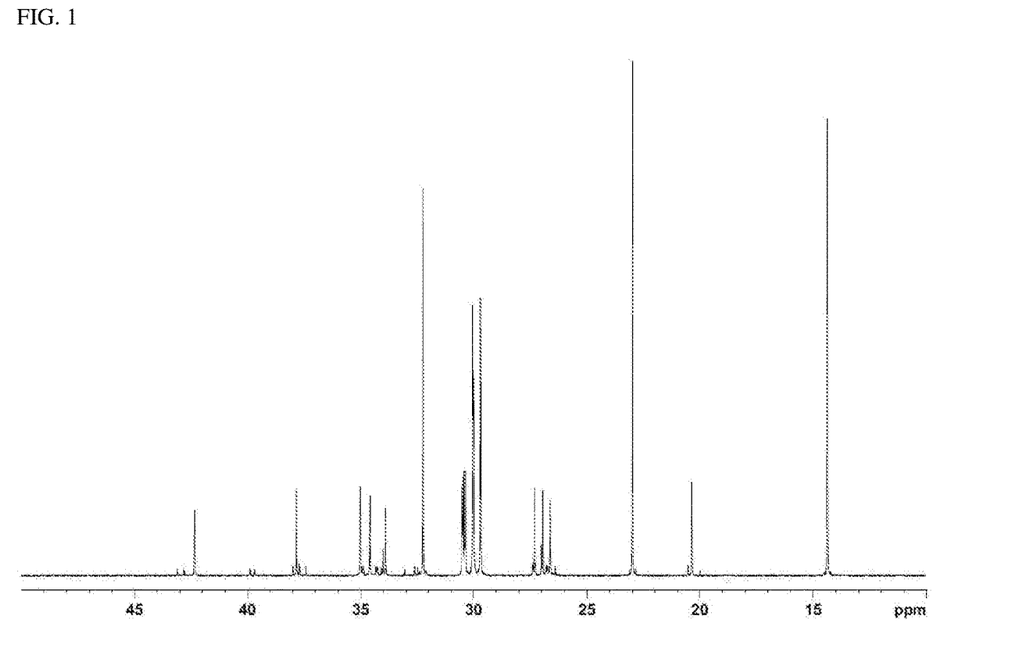
FIG. 1 is a graph showing the carbon NMR spectrum of a decene oligomer polymerized using a metallocene catalyst.
Figure 2:
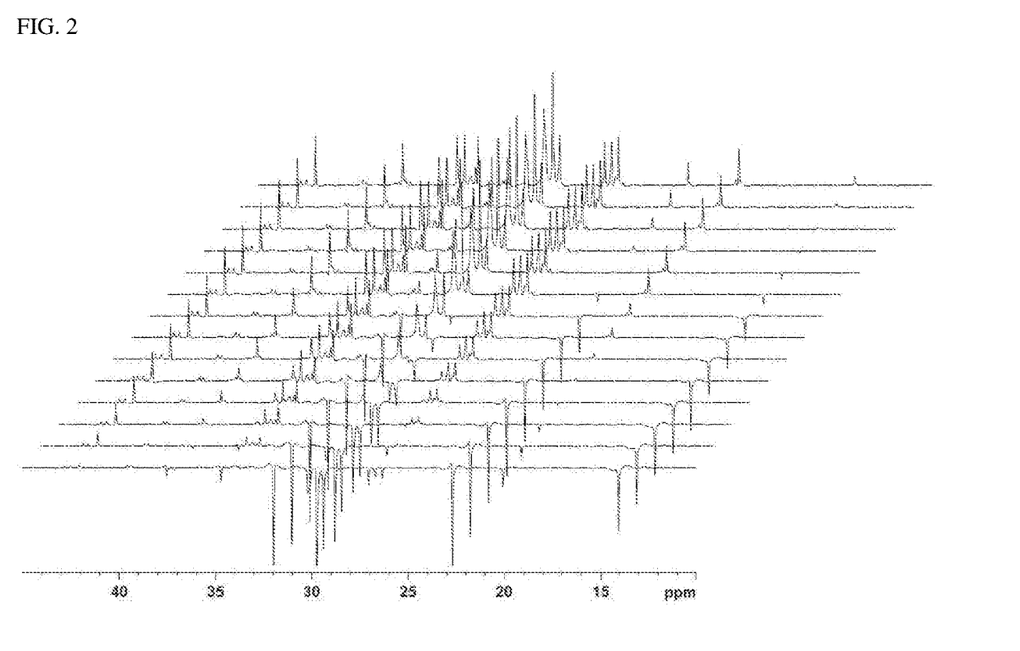
FIG. 2 is a graph showing the T1 inversion recovery power gated (T1IRPG) decoupling 2D experiment spectrum of a decene oligomer polymerized using the metallocene catalyst of Example 1.
Figure 3:
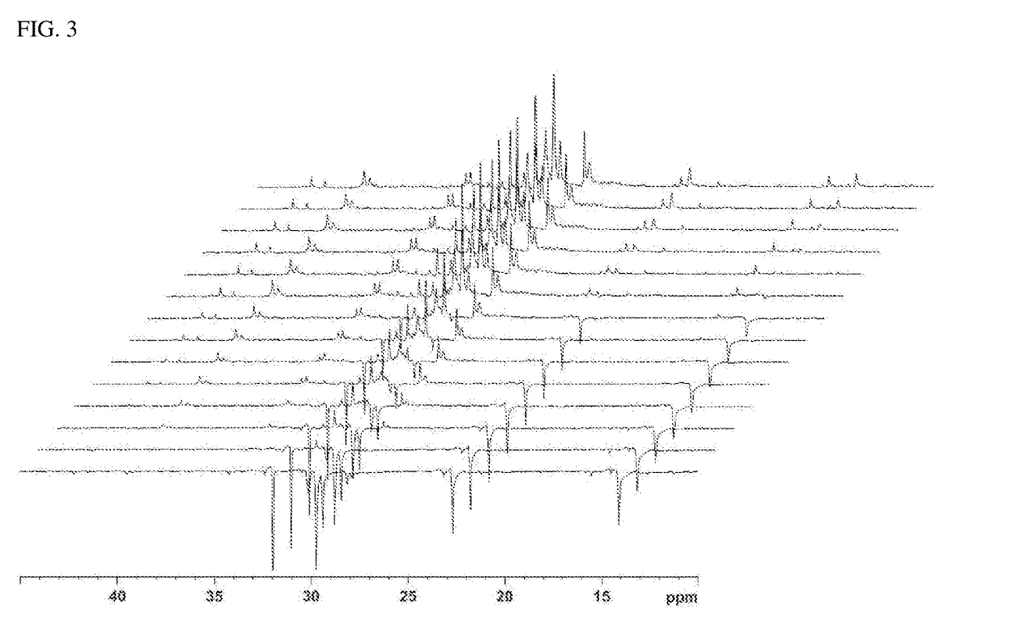
FIG. 3 is a graph showing the T1IRPG decoupling 2D experiment spectrum of a decene oligomer polymerized using the cation catalyst of Comparative Example 1.

Moreover, the $T_1$ relaxation time measurement spectrum of the alphaolefin oligomer of Example 1 is shown in FIG. 2, and the $T_1$ relaxation time measurement spectrum of the alphaolefin oligomer of Comparative Example 1 is shown in FIG. 3. Here, the spectral results were obtained using pulse sequences of T1IRPG (T1 Inversion Recovery Power Gated) decoupling 2D experiment, and τ (the time between 1800 pulse and 900 pulse) is 0.3 to 1.0 sec and 1.5 to 2.0 sec (0.1 second interval).

TABLE 3

Carbon Peak (ppm)

| Position | Kind | Example 1 | Example 2 | Example 3 | C. Example 1 | C. Example 2 |
|---|---|---|---|---|---|---|
| A1 | $CH_3$ | 14-15 | 14-15 | 14-15 | 14-15 | 14-15 |
| A2 | $CH_2$ | 22-24 | 22-24 | 22-24 | 22-24 | 22-24 |
| B1 | $CH_3$ | 19-21 | 19-21 | 19-21 | 16-17 | 16-17 |
| B2 | CH | 34-35 | 34-35 | 34-35 | 34-35 | 34-35 |
| B3 | $CH_2$ | 42-43 | 42-43 | 42-43 | 40-43 | 40-43 |

TABLE 4

| $T_1$ Relaxation time | Example 1 | Example 2 | Example 3 | Comparative Example 1 | Comparative Example 2 |
|---|---|---|---|---|---|
| A1 | 2.54 | 2.54 | 2.46 | 2.25 | 2.32 |
| A2 | 2.32 | 2.32 | 2.25 | 2.17 | 2.17 |
| B1 | 0.94 | 0.94 | 0.72 | 1.01 | 1.01 |
| B2 | 0.50 | 0.50 | 0.36 | 0.65 | 0.65 |
| B3 | 0.29 | 0.29 | 0.29 | 0.65 | 0.65 |

As is apparent from Tables 3 and 4, based on the results of measurement of $T_1$ relaxation time of the oligomers of Examples 1 to 3 and Comparative Examples 1 and 2, the results of Examples 1 to 3 were similar to those of Comparative Examples 1 and 2.

Furthermore, the oligomers prepared in Examples showed higher values of the ends A1 and A2 of the terminal chain than those of the oligomers prepared in Comparative Examples, indicating that the chain is longer and the mobility of the terminal group is higher.

In contrast, the oligomers prepared in Examples showed lower values of the molecular centers B1, B2 and B3 than those of the oligomers prepared in Comparative Examples, indicating that the central carbon atoms have lower mobility, that is, are more rigid.

Specifically, in the oligomers having a kinematic viscosity at 100° C. of 3.7 to 4.3 cSt (Examples 1 and 2), the carbon at position B1 had a $T_1$ relaxation time of less than 1.0, as measured by the NMR pulse sequence, and the carbons at positions B2 and B3 had a $T_1$ relaxation time of less than 0.6. Furthermore, the carbon at position A1 had a $T_1$ relaxation time of 2.4 or more, and the carbon at position A2 had a $T_1$ relaxation time of 2.2 or more.

In the oligomer having a kinematic viscosity at 100° C. of 5.6 to 6.4 cSt (Example 3), the carbon at position B1 had a $T_1$ relaxation time of less than 0.85, the carbons at positions B2 and B3 had a $T_1$ relaxation time of less than 0.55, and the carbons at positions A1 and A2 had a $T_1$ relaxation time of 2.4 or more and a $T_1$ relaxation time of 2.2 or more, respectively.

4. Branch Ratio

As the structural properties of the alphaolefin oligomers of Examples 1 to 3 and Comparative Examples 1 and 2, the branch ratio depending on the amounts of $CH_2$ and $CH_3$ was measured. The results are shown in Table 5 below.

The relative amounts of $CH_2$ and $CH_3$ were measured through hydrogen NMR, and based on 7.24 ppm of chloroform, $CH_2$ was represented as an integral of 0.95 to 1.60 ppm, and $CH_3$ was represented as an integral of 0.75 to 0.95 ppm. More specifically, the integral of $CH_3$ is 1.

The branch ratio is obtained by dividing the amount of the $CH_3$ group in the molecular structure by the amount of the $CH_2$ group, and is represented below.

$$\text{Branch ratio} = P1/P2 \qquad (1)$$

(Here, P1 is the amount of $CH_3$ group and P2 is the amount of $CH_2$ group, the amounts of $CH_2$ and $CH_3$ groups being measured through $^1$H-NMR.)

TABLE 5

| Regularity | | Example 1 | Example 2 | Example 3 | Comparative Example 1 | Comparative Example 2 |
|---|---|---|---|---|---|---|
| Molar Ratio ($CH_3$:$CH_2$) | Experimental value (NMR) | 1:4.49 | 1:4.28 | 1:4.74 | 1:3.62 | 1:3.64 |
| $CH_3$Gr. (wt %) | Experimental value (NMR) | 0.1821 | 0.1894 | 0.1742 | 0.2165 | 0.2155 |
| Branch Ratio | Experimental value (NMR) | 0.2227 | 0.2336 | 0.2109 | 0.2762 | 0.2747 |

As is apparent from Table 5, the molar ratio of $CH_3$ to $CH_2$ was lower in the alphaolefin oligomers prepared in Examples than in the alphaolefin oligomers prepared in Comparative Examples, indicating that there are few branches in the molecular structure, which can also be confirmed by the branch ratio. In conclusion, as the number of branches in the molecular structure was smaller, superior oxidative stability, a high viscosity index, a lower or similar pour point and low Noack volatility were exhibited, indicative of improved properties.

Although preferred embodiments of the present invention have been disclosed for illustrative purposes, those skilled in the art will appreciate that various modifications are possible without departing from the scope and spirit of the invention as disclosed in the accompanying claims, and such modifications should not be understood separately from the technical ideas or essential characteristics of the present invention.

What is claimed is:

1. A hydrogenated alphaolefin oligomer composition comprising at least one hydrogenated alphaolefin oligomer, the at least one hydrogenated alphaolefin oligomer having a molecular structure with a weight average molecular weight of 697 to 1300 and having a branch ratio of 0.265 or less as represented by Equation (1) below

$$\text{Branch ratio} = P1/P2 \qquad (1)$$

wherein P1 is an amount of a $CH_3$ group and P2 is an amount of a $CH_2$ group, the amount of the $CH_2$ group and the amount of the $CH_3$ group being measured through $^1$H-NMR, wherein the at least one hydrogenated alphaolefin oligomer has a kinematica viscosity at 100° C. of 6.3 cSt or less and has a viscosity index of 134.1 or more.

2. The hydrogenated alphaolefin oligomer composition of claim 1, wherein the at least one hydrogenated alphaolefin oligomer is configured such that carbon at position B2 in Structural Formula 1 below has a $T_1$ relaxation time of less than 0.6 at 298 K as measured by an NMR pulse sequence

[Structural Formula 1]

wherein n=1 to 9.

3. The hydrogenated alphaolefin oligomer composition of claim 2, wherein carbon at position B3 of the at least one hydrogenated alphaolefin oligomer has a $T_1$ relaxation time of less than 0.5 at 298 K as measured by the NMR pulse sequence.

4. The hydrogenated alphaolefin oligomer composition of claim 2, wherein carbon at position B3 of the at least one hydrogenated alphaolefin oligomer is tertiary carbon (CH group) or secondary carbon ($CH_2$ group).

5. The hydrogenated alphaolefin oligomer composition of claim 2, wherein carbon at position A1 of the at least one hydrogenated alphaolefin oligomer has a $T_1$ relaxation time of 2.35 or more at 298 K as measured by the NMR pulse sequence.

6. The hydrogenated alphaolefin oligomer composition of claim 2, wherein carbon at position A2 of the at least one hydrogenated alphaolefin oligomer has a $T_1$ relaxation time of 2.20 or more at 298 K as measured by the NMR pulse sequence.

7. The hydrogenated alphaolefin oligomer composition of claim 1, wherein the at least one hydrogenated alphaolefin oligomer has a flash point of 235° C. or more.

8. The hydrogenated alphaolefin oligomer composition of claim 1, wherein the at least one hydrogenated alphaolefin oligomer has a Noack volatility of less than 12%.

9. The hydrogenated alphaolefin oligomer composition of claim 1, wherein the at least one hydrogenated alphaolefin oligomer has a pour point of −50° C. or less.

10. The hydrogenated alphaolefin oligomer composition of claim 1, wherein the at least one hydrogenated alphaolefin oligomer has a kinematic viscosity at 100° C. of 6.3 cSt or less.

11. The hydrogenated alphaolefin oligomer composition of claim 1, wherein the at least one hydrogenated alphaolefin oligomer has a kinematic viscosity at 40° C. of 35.0 cSt or less.

12. The hydrogenated alphaolefin oligomer composition of claim 1, wherein the at least one hydrogenated alphaolefin oligomer contains 0.1 to 3.5 wt % of a dimer.

13. A lubricant composition comprising the hydrogenated alphaolefin oligomer composition of claim 11.

* * * * *